United States Patent
Opfermann et al.

(10) Patent No.: US 7,038,209 B2
(45) Date of Patent: May 2, 2006

(54) DEVICE FOR DETECTING THERMAL CONDUCTIVITY BY MEANS OF OPTICAL PULSES

(75) Inventors: Johannes Opfermann, Selb (DE); Juergen Blumm, Selb (DE)

(73) Assignee: NETZSCH-Geraetebau GmbH, Selb (DE)

( * ) Notice: Subject to any disclaimer, the term of this patent is extended or adjusted under 35 U.S.C. 154(b) by 46 days.

(21) Appl. No.: 10/654,780

(22) Filed: Sep. 4, 2003

(65) Prior Publication Data

US 2004/0079886 A1    Apr. 29, 2004

(30) Foreign Application Priority Data

Sep. 13, 2002   (DE) ................. 102 42 741

(51) Int. Cl.
  *G01J 5/02*   (2006.01)
  *G01N 25/20*  (2006.01)
  *G01N 25/18*  (2006.01)
  *G01K 17/00*  (2006.01)

(52) U.S. Cl. .............. 250/341.6; 374/43; 374/44; 702/136

(58) Field of Classification Search ............. 250/341.6, 250/340, 341.1, 341.5, 351; 702/30, 136; 374/43, 44
See application file for complete search history.

(56) References Cited

U.S. PATENT DOCUMENTS 4,928,254 A * 5/1990 Knudsen et al. ............ 702/136
5,713,665 A   2/1998 Kato et al.
6,273,603 B1 * 8/2001 Cheindline et al. ........... 374/43

FOREIGN PATENT DOCUMENTS

DE    33 17 513   11/1984
JP    8-261967    10/1996

OTHER PUBLICATIONS

Blumm, J. and Opfermann, J. "Improvement of the Mathematical Modeling of Flash Measurements", High Temperatures High Pressures (UK), vol. 34, No. 5 (2002), pp. 515-521.*

Blumm, J. and Lemarchand, S. "Influence of Test Conditions on the Accurancy of Laser Flash Measurements", High Temperatures High Pressures (UK), vol. 34, No. 5 (2002), pp. 523-528.*

Baba, T. and Ono, A. "Improvement of the Laser Flash Method to Reduce Uncertainty in Thermal Diffusivity Measurements", Measurement Science and Technology (UK), vol. 12, No. 12(Dec. 2001), pp. 2046-2057.*

(Continued)

*Primary Examiner*—David Porta
*Assistant Examiner*—Frederick F. Rosenberger
(74) *Attorney, Agent, or Firm*—Kevin L. Daffer; Daffer, McDaniel, LLP (57) ABSTRACT

The present invention relates to a device for detecting the thermal conductivity by application of optical pulse techniques. A sample preheated in a furnace is exposed to energy by means of an optical pulse. The temperature profile in the sample is recorded by means of an infrared sensor. The thermal conductivity of the sample can then be detected by mathematical derivation. To reduce tho influence of the time history of the optical pulse on measurement, a measuring means is provided for determining this history, An analyzer unit then derives therefrom the corrected temperature profile.

12 Claims, 3 Drawing Sheets

OTHER PUBLICATIONS

Vozar, L. et al. Flash Method of Measuring the Thermal Diffusivity—a Review. High Temperatures High Pressures, vol. 35-36, No. 3 (2003-2004), pp. 253-264.*

Xue, J. et al. The Effects of a Finite Pulse Time in the Flash Thermal Diffusivity Method. International Journal of Thermophysics, vol. 14, No. 1 (Jan. 1993), pp. 123-133.*

Dusza, L. Combined Solution of the Simultaneous Heat Loss and Finite Pulse Corrections with the Laser Flash Method. High Temperatures High Pressures, vol. 27-28, No. 5 (1995-1996), pp. 467-473.*

Larson et al., "Correction for Finite-Pulse-Time Effects in Very Thin Samples using the Flash Method of Measuring Thermal Diffusivity," Journal of Applied Physics, vol. 38, No. 2, 1967, pp. 465-474.

Cape et al., "Temperature and Finite-Pulse-Time Effects in the Flash Method for Measuring Thermal Diffusivity," Journal of Applied Physics, vol. 34, No. 7, 1963, pp. 1909-1913.

Cowan, "Pulse Method of Measuring Thermal Diffusivity at High Temperatures," Journal of Applied Physics, vol. 34, No. 4, Part 1, 1963, pp. 926-927.

Mehling et al., "Thermal Diffusivity of Semitransparent Materials Determined by the Laser-Flash Method Applying a New Analytical Model," International Journal of Thermophysics, vol. 19, No. 3, 1998, pp. 941-949.

* cited by examiner

DEVICE FOR DETECTING THERMAL CONDUCTIVITY BY MEANS OF OPTICAL PULSES

FIELD OF THE INVENTION

The present invention relates to a device for detecting thermal conductivity by optical pulse techniques.

PRIOR ART

Various devices for determining the thermal conductivity by optical pulse techniques have become known. For example, the German Patent DE 33 17 513 C2 describes a device of the claimed general type, wherein energy is supplied to a sample by laser pulses. The infrared radiation emitted by the sample is measured by means of a pyrometer. To maintain those effects at a constant level, which are produced by the laser pulses on the measuring result, a time-limiting camera release is disposed between the laser and the sample. This camera release ensures at least a reproducible pulse shape. This device entails the disadvantage, however, that in the case of long pulses or extremely thin and thermally conductive samples, the results of measurement are falsified by the pulse shape of the laser.

The U.S. Pat. No. 4,928,254 discloses a device for and a method of detecting the thermal conductivity by application of an optical pulse method. There, a sample is irradiated with a succession of optical pulses from a YAG laser. A sensor is used to detect the infrared radiation emitted by the sample. Then, the thermal conductivity is calculated by deriving it from the result of measurement by means of a computer. Moreover, a certain fraction is decoupled from the laser beam and supplied to a photo diode. The computer can then determine the number of laser pulses issued on the basis of the signal from the photo diode. In this method, too, the shape of the laser pulses is left out of consideration.

The European standard EN 821–2 establishes a maximum period of a laser pulse at 1% of the half-rise time (the period elapsing until 50% of the maximum signal level is reached) of the detection signal of the infrared sensor in order to avoid a high impairment of the result of measurement beyond proportion, which is caused by the influences taken by the pulse lengths of the laser pulses.

In order to permit also measurements with longer laser pulses or in cases of a higher thermal conductivity, the pertinent literature proposes the approximation of the laser pulse and the correction of the detected curve shape of the infrared sensor by performing a convolution with the approximated laser pulse. A particularly expedient approximation technique is proposed by Larson and Koyama in: Journal of Applied Physics, 38 (1967), p. 465. According to that publication, an exponential form of the curve shape of the laser pulse is assumed. With this approximation in correspondence with the European Standard EN 821–2, it is possible to realize a maximum period of a laser pulse, which corresponds to 10% of the half-rise time of the measuring signal of the infrared sensor. Measurement in a range going therebeyond is not possible at present.

BRIEF DESCRIPTION OF THE INVENTION

The present invention is based on the problem of improving a device for or a method of detecting the thermal conductivity by means of optical pulse techniques in such a way that even in the case of comparatively long optical pulses as well as extremely thin samples or of an extremely high thermal conductivity, measurements can be performed. This relates particularly to the range in which the maximum period of a laser pulse exceeds 10% of the rise time of the measuring signal of the infrared sensor.

In accordance with the present invention, this problem is solved by the provisions defined in the independent claims. Expedient improvements of the invention are the subject matters of the dependent claims.

Figure 1:
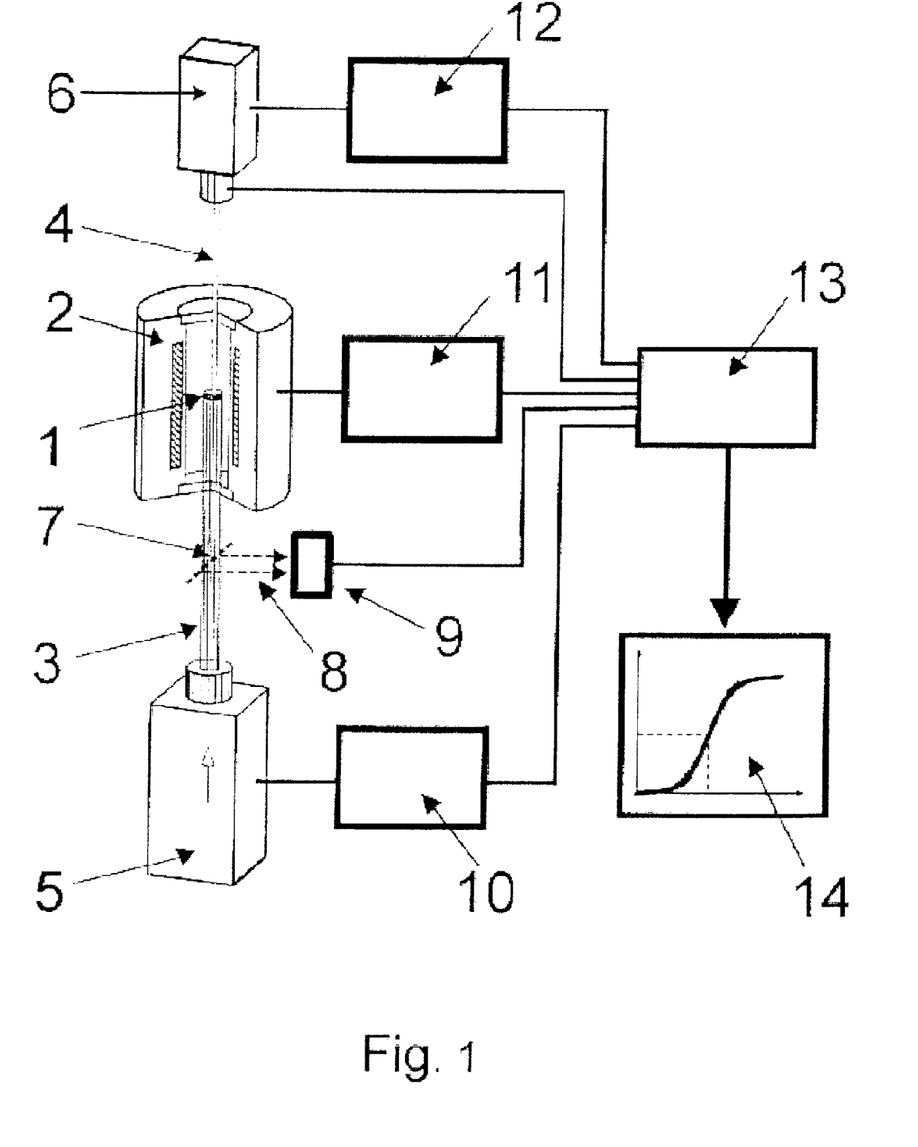
FIG. 1 is a general schematic view of an inventive device.

An inventive device for detecting the thermal conductivity of a sample (1) comprises a furnace (2) for heating the sample to a previously selected temperature. Moreover, a source of radiation or light source (5) is provided, preferably in the form of a laser or a flashlight for emitting radiation (3) for heating the sample. It is equally possible to emit also any other kind of electromagnetic radiation instead of light. The radiation is preferably emitted in the form of short pulses. The energy absorbed in the sample results in heating of the sample. In correspondence therewith, the infrared radiation (4), which is emitted by the sample, varies, too. The time history of this infrared radiation is detected by means of an infrared sensor (6). The signal from the infrared sensor (6) is supplied, via a signal amplifier (12), to an analyzer unit (13). This analyzer unit is so designed that is determines the thermal conductivity of the sample by deriving it from the time history of the sensor signal. For adjustment of the result of measurement by elimination of falsifications caused by the time history of the optical pulse, a device is provided for measuring the time history of the optical pulse. This device comprises a decoupling element (7) such as a semi-transparent mirror that decouples a predetermined fraction of the radiation of the light source (5) as a reference radiation and supplies the latter to a sensor (9) for measuring the laser radiation. This value so measured is then supplied to the analyzer unit (13) for detecting the time history of the optical pulse. In order to achieve a sufficient resolution of the sensor it is necessary that the sensor has a bandwidth in correspondence with the invention, which is substantially wider than the reciprocal value of the pulse length of the radiation pulse. The bandwidth wider by more than a factor of 10 than the reciprocal value of the pulse length is preferred. The time history of the radiation pulse is expediently detected by digitizing and storing the measured values. The duty cycle must be selected here in such a manner that a sufficient number of measured values is determined, preferably at least ten values, throughout the period of the radiation pulse. The analyzer unit is so designed for determining the thermal conductivity that it corrects initially the signal measured by the infrared sensor (6) by application of the signal of the sensor (9) for measuring the laser radiation.

Tests have shown that with such a correction the ratio of the pulse length of the laser pulse to the half-rise time of the measuring signal can be extended up to a value of 0.75. Consequently, the measuring range can be widened by a factor higher than 7, compared against a correction in compliance with the standard EN 821–2.

With such an inventive correction it has now become possible for the first time to measure multi-layer samples with a high precision.

It is, of course, also possible to provide a device for cooling the sample, instead of the furnace (1). For simplification of the representation, the term "furnace" is referred to in this document because in the majority of applications such a furnace is actually provided. Such a furnace serves, however, the function of maintaining the temperature in the environment of the sample at a constant predetermined value.

Furthermore, the analyzer unit (13) is designed for correcting the signal measured by the infrared sensor (6) by performing a convolution with the signal of the sensor (9) for measuring the laser radiation. This provision preferably serves to achieve the normalization to a corresponding comparative signal that relates to an excitation by an ideal laser pulse in the form of a Dirac pulse.

In addition, the analyzer unit (13) presents a configuration for approximation of the laser pulse by sections. In this technique, the laser pulse is approximated in at least two sections by means of exponential functions. With typical laser pulses, the time history can be subdivided into the following sections:

(a) a high-speed rise starting section
(b) a generally slightly downward sloping plateau section, and
(c) a high-speed decay section following the cut-off of the pumping light.

In correspondence with the curve shape or the duration of the laser pulse relative to the rise times and the decay times, this pulse can be advantageously approximated by defining the sections (a), (b), (c) or, in the event of short laser pulses, only defining the sections (a) and (b). As a matter of course, in the case of particularly complex pulse shapes, it is also possible to approximate a laser pulse also by the subdivision into further sections.

According to the invention, the analyzer unit (13) is designed for determining the difference in Delay between the rated zero point in time and the starting time of the optical pulse.

Another embodiment of the analyzer unit (13) consists in the provision that for approximation of the intensity of the laser pulse $I_1(t)$ during the rapidly rising edge the following formula is used as a function of the time t:

$$I_1(t) = A \cdot [1 - \exp\{-(t-\text{Delay})/\tau_1\}]$$

wherein:
A: scaling factor
Delay: time delay of the starting point of the upward edge relative to a zero point in time
$\tau_1$: time constant of the rising ramp The variables of this function and the functions described below are determined by derivation from the measured signals of the signal of the sensor (9) for measuring the laser radiation. In general, good results are achieved already with this single-term formula.

As a matter of fact, an improvement of the results can be achieved by application of the following formula for $I_1(t)$:

$$I_1(t) = A \cdot \left[ 1 - \frac{\tau_{12}}{\tau_{12} - \tau_{11}} \cdot \exp\{-(t-\text{Delay})/\tau_{12}\} + \frac{\tau_{11}}{\tau_{12} - \tau_{11}} \cdot \exp\{-(t-\text{Delay})/\tau_{11}\} \right]$$

wherein
Delay: time delay of the starting point of the upward edge relative to a zero point in time
$\tau_{11}$: first time constant of the rising ramp
$\tau_{12}$: second time constant of the rising ramp A further configuration of the analyzer unit (13) consists in the provision that for approximation of the intensity of the laser pulse $I_2(t)$ during the generally slightly downward sloping plateau the following formula is applied as a function of time t:

$$I_2(t) = I_1(t) \cdot \exp\{-(t-\text{Delay})/\tau_2\}$$

wherein
$I_1(t)$: formula for defining the intensity of the laser pulse during the rising edge
Delay: time delay of the starting point of the rising edge relative to a zero point in time
$\tau_2$: time constant of the rising ramp $I_1(t)$ is an optional term defining the previous time history of the intensity of the laser pulse. Preferably, one of the above-presented formulae is applied here.

Another embodiment of the analyzer unit (13) consists in the provision that for approximation of the intensity of the laser pulse $I_3(t)$ during the high-speed downward edge, after cut-off of the pumping light, the following formula is applied as a function of time t:

$$I_3(t) = I_2(t = \text{Delay} + t_e) \cdot \exp\{-(t-\text{Delay}-t_e)/\tau_3\}$$

wherein
$I_2(t)$: formula defining the previous time history of the intensity of the laser pulse
Delay: time delay of the starting point of the upward edge relative to a zero point in time
$t_e$: difference in time between the beginning of the downward edge and the beginning of the upward edge
$\tau_3$: time constant of the downward edge.

$I_2(t)$ is an optional term defining the previous time history of the intensity of the laser pulse. Here, one of the formulae presented above should be applied.

An improvement of the results can be achieved by the application of the following formula for $I_3(t)$:

$$I_3(t) = I_2(t = \text{Delay} + t_e) \cdot \left[ \frac{\tau_{32}}{\tau_{32} - \tau_{31}} \cdot \exp\{-(t-\text{Delay}-t_e)/\tau_{32}\} - \frac{\tau_{31}}{\tau_{32} - \tau_{31}} \cdot \exp\{-(t-\text{Delay}-t_e))/\tau_{31}\} \right]$$

wherein
$I_2(t)$: formula defining the previous time history of the intensity of the laser pulse
Delay: time delay of the starting point of the upward edge relative to a zero point in time
$t_e$: difference in time between the beginning of the downward edge and the beginning of the upward edge
$\tau_{31}$: first time constant of the downward edge
$\tau_{32}$: second time constant of the downward edge $I_2(t)$ is an optional term defining the previous time history of the intensity of the laser pulse. Preferably, one of the formulae presented above should be applied here.

A further embodiment of the invention provides for the analyzer unit (13) to be designed so that it uses approximations of the optical pulse when performing a convolution with model functions E(t) for heat transfer for the determination of the heat transfer function R(t):

$$R(t) = \int_0^t I(s) \cdot E(t-s) ds$$

wherein
I(t): pulse profile of the laser pulse
E(t): model function for heat transfer Then, the thermal conductivity can be determined by deriving it from the heat transfer function R(t). For defining the function of the pulse profile I(t) of the laser pulse one or several ones of the aforedescribed approximations are applied.

In another expedient embodiment of the invention, the analyzer unit (13) is configured for performing a convolution of the optical pulse with a model function using the Cowan approximation. The Cowan approximation, published in the Journal of Applied Physics 34 (1963), p. 926—with the essence of this publication constituting part of this document—is based on the following heat transfer equation E(t) as a function of time t:

$$E(t) \approx \exp\left(-\frac{k\alpha}{l^2}t\right) \cdot \left[1 + 2\sum_{n=1}^{\infty}(-1)^n \exp\left(\frac{-\alpha n^2 \pi^2}{l^2}t\right)\right]$$

wherein
k: coefficient descriptive of the thermal losses
α: thermal conductivity
l: thickness of the sample The approximation indicated here starts initially out from a rectangular shape of the laser pulse. In combination with the aforedescribed approximations for the shape of the laser pulse, an improved precision can be achieved.

A further configuration of the analyzer unit (13) consists in its design for translucent materials, with application of a heat transfer solution proposed by Mehling et al. in: International Journal of Thermophysics 19 (1998) p. 941—with the essence of that publication constituting part of this document:

$$E(t) = 2T_\infty \sum_{n=1}^{\infty} l\beta_n \exp(\alpha\beta_n t) \frac{l\beta_n \cos(l\beta_n) + lh\sin(l\beta_n)}{l^2(\beta_n^2 + h^2) + 2lh}$$

wherein
$T_\infty$: sample temperature in thermal balance
l: thickness of the sample
$\beta_n$: the positive roots of the equation $$\tan(l\beta_n) = \frac{2h\beta_n}{\beta_n^2 - h^2}$$

$$\beta_1 = 0$$

h: radiation losses of the sample with $$h = \frac{4\sigma\varepsilon T_{sur}^3}{\kappa}$$

wherein
σ: Boltzmann's constant
ε: emission constant of the sample
$T_{sur}$: ambient temperature
κ: constant of thermal conductivity At temperature differences between the face and the rear side of the sample, which are smaller than the sample temperature, the following values apply for h:

$$h = \begin{cases} h & \text{for even } n \\ h(1+2\eta) & \text{for odd } n \end{cases}$$

wherein
η: parameter characterizing the transparency of the sample.

With additional modeling of the thermal losses, in analogy with Cowan's proposal, the following equation is achieved:

$$E(t) = 2T_\infty \exp(-k\alpha t/l^2) \sum_{n=1}^{\infty} l\beta_n \exp(-\alpha\beta_n t) \frac{l\beta_n \cos(l\beta_n) + lh\sin(l\beta_n)}{l^2(\beta_n^2 + h^2) + 2lh}$$

A further embodiment of the analyzer unit (13) consists in a configuration of the analyzer unit with application of a heat transfer E(r,t) solution published by Cape and Lehmann in: Journal of Applied Physics 34 (1963) p. 1909 —with the essence of that publication constituting part of this document. In that solution, not only the thermal losses via the face and rear side (facial thermal losses) but also the thermal losses via the cylinder wall are considered (radial heat losses).

$$E(r,t) = \sum_{m=0}^{\infty} C_m X_m \sum_{i=0}^{\infty} D_i(r, Y_r) \int_0^t I(s) \exp\left(-\frac{a\pi^2}{d^2}\omega_{im}(t-s)\right) ds$$

wherein $$C_m = \frac{(-1)^m (2a/d) X_m}{X_m^2 + 2Y_X + Y_X^2}$$

$$D_i(r, Y_r) = \frac{2Y_r}{Y_r^2 + z_i^2} \cdot \frac{J_0(z_i \cdot (r/r_0))}{J_0(z_i)}$$

$$\omega_{im} = (l/\pi)^2 (X_m^2/d^2 + z_i^2/r_0^2)$$

$X_m$: roots of the equation $(X_m^2 - Y_x^2)\tan X_m = 2X_m Y_X$
$z_i$: roots of the equation $Y_r \cdot J_0(z_i) = z_i \cdot J_1(z_i)$
$Y_x$: facial thermal loss
$Y_r$: radial thermal loss
$J_k$: Bessel function of the order k
r: distance from the centre
$r_0$: diameter of the sample Another embodiment of the analyzer unit (13) consists in a design of the analyzer unit for the application of a model function of the heat transfer in the case of multiple layers, preferably double or triple layers, respectively. Here, the thermal conductivity of one layer may be unknown.

A further embodiment of the analyzer unit (13) consists in a design of the analyzer unit for the application of a model function for the heat transfer with thermal resistance in the case of multiple layers, preferably double or triple layers, respectively.

A further embodiment of the invention provides for an analyzer unit that is designed to perform a convolution by way of subtraction of the spectrally transformed measured values and subsequent re-transformation. Appropriate spectral transformation techniques are the fast Fourier transform or also the Laplace transform.

DESCRIPTION OF THE DRAWINGS

In the following, the invention will be described by exemplary embodiments, without any limitation of the general inventive idea, with reference to the drawings.

FIG. 1 shows an exemplary embodiment of the inventive device. A sample (1) is heated to a preselected temperature in a furnace (2). To measure the thermal conductivity at this temperature, the sample is exposed to the energy of a highly efficient light source light (3) in the form of short pulses. The energy absorbed by the sample results in heating the latter. In correspondence therewith, the infrared radiation (4) emitted by the sample changes. This infrared radiation is detected by means of an infrared sensor (6) over its time history. The signal of the infrared sensor (6) is supplied to an analyzer unit (13) by means of a signal amplifier (12). This analyzer unit is so designed that it derives from the time history of the sensor signal the thermal conductivity of the sample. For adjusting the measuring result by elimination of falsifications induced by the time history of the optical pulse, a device is provided for measuring the time history of the optical pulse. This device comprises a decoupler element (7) such as a semi-transparent mirror that decouples a predetermined fraction of the radiation from the light source (5) as reference radiation (8) and supplies the reference to sensor (9) for measuring the laser radiation. This measured value is then supplied to the analyzer unit (13) for determination of the time history of the optical pulse. The analyzer unit corrects the signal detected by the infrared sensor (6) by performing a convolution with the signal detected by the sensor (9) for measuring the laser radiation. A display unit (14) is provided for displaying the result.

Figure 2:
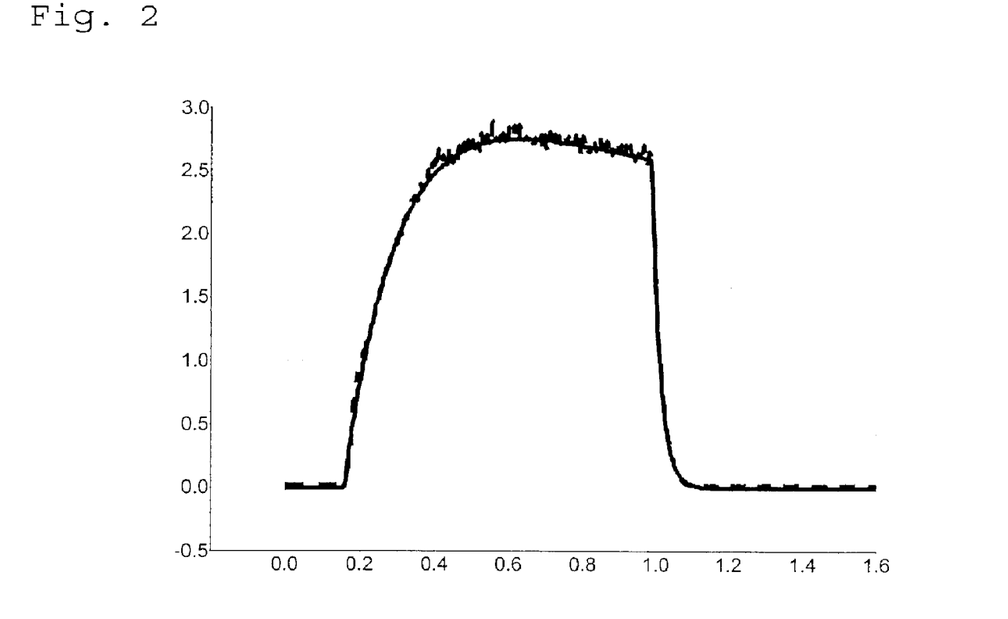
FIG. 2 illustrates a typical laser pulse of major length.

FIG. 2 shows a typical laser pulse of major length. The time unit ms is plotted along the horizontal axis. The vertical axis reflects the intensity of the pulse in standardized units. The illustrated laser pulse has a rated pulse length of 1.0 ms. In such a pulse, three sections can be distinguished. It presents (a) a high-speed rising starting section (b) a generally slightly downward sloping plateau, and (c) a high-speed downward slope after cut-off of the pumping light.

These sections are now approximated by individual functions.

Figure 3:
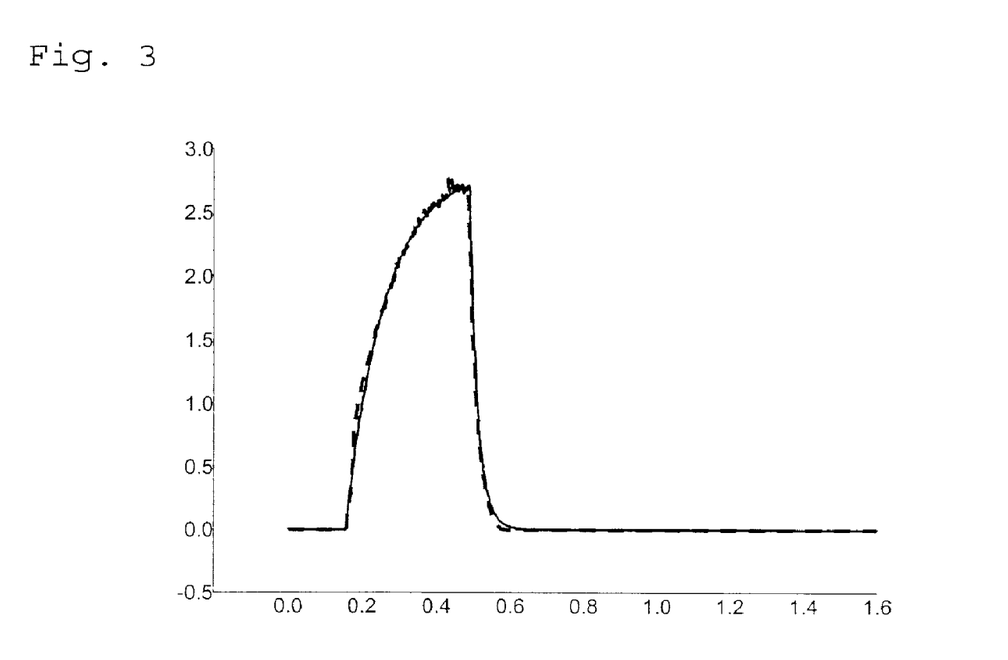
FIG. 3 shows a typical laser pulse of medium length.

FIG. 3 illustrates a typical laser pulse of medium length. The time is plotted in ms along the horizontal axis. The vertical axis reflects the intensity of the pulse in standardized units. The illustrated laser pulse presents a rated pulse length of 0.5 ms. In such a pulse, only two sections (a) and (c) can still be recognized. This pulse can be expediently approximated in two segments.

Figure 4:
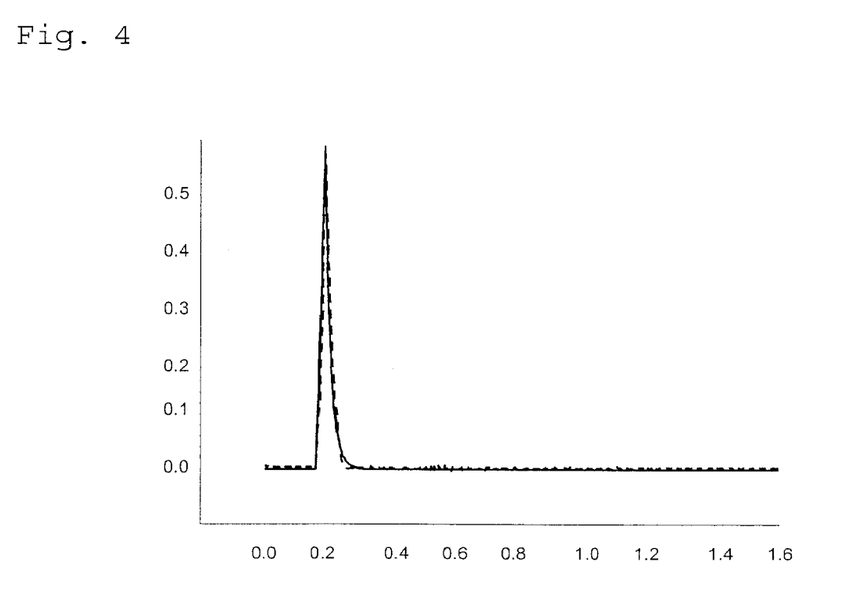
FIG. 4 is an illustration of a typical laser pulse of short length.

FIG. 4 shows a typical laser pulse of short length. The time is plotted in ms units along the horizontal axis. The vertical axis reflects the intensity of the pulse in standardized units. The illustrated laser pulse has a rated pulse length of 0.2 ms. In such a pulse, one can only distinguish still two sections (a) and (c). This pulse can be expediently approximated in two segments.

LIST OF REFERENCE NUMERALS 1 sample
2 furnace
3 radiation for heating the sample
4 infrared radiation emitted by the sample
5 source of radiation
6 infrared sensor
7 decoupler element
8 reference radiation
9 sensor for measuring the reference radiation
10 Laser power unit
11 furnace power unit
12 signal amplifier
13 analyzer unit
14 display unit

The invention claimed is:

1. Device for detecting thermal conductivity of a sample by application of optical pulse techniques, comprising
   a furnace for heating the sample to a predetermined temperature,
   a source of radiation for emitting high-energy radiation in the form of pulses onto said sample for heating the sample,
   an infrared sensor for detecting time history of infrared radiation emitted by said sample,
   a decoupler element for decoupling a reference radiation from a beam emitted by said source of radiation,
   a second sensor for measuring said reference radiation, as well as
   an analyzer unit for detecting the thermal conductivity of the sample by analyzing signals of said infrared sensor,
   said second sensor for measuring said reference radiation having a bandwidth that is substantially wider than a reciprocal value of pulse length of said source of radiation,
   said analyzer unit being so designed that it detects the thermal conductivity by deriving it from the signals of said infrared sensor, which are corrected by performing a convolution with the measuring signals of said second sensor by approximating a laser pulse by sections in at least two sections by means of exponential functions, and
   said analyzer unit being designed for detecting a time difference between a rated zero point in time and a starting point of the approximated laser pulse.

2. Device according to claim 1,
   characterized in that
   said analyzer unit is designed for approximating a high-speed rising edge of the laser pulse by the formula $I_1(t)=A\cdot[1-\exp\{-(t-\text{Delay})/\tau_1\}]$ 3. Device according to claim 1,
   characterized in that
   said analyzer unit is designed for approximating a high-speed rising edge of the laser pulse by the formula $$I_1(t) = A \cdot \left[ 1 - \frac{\tau_{12}}{\tau_{12} - \tau_{11}} \cdot \exp\{-(t - \text{Delay})/\tau_{12}\} + \frac{\tau_{11}}{\tau_{12} - \tau_{11}} \cdot \exp\{-(t - \text{Delay})/\tau_{11}\} \right].$$

4. Device according to claim 3,
characterized in that
said analyzer unit is designed for approximating a slightly downward sloping plateau of the laser pulse by the formula $$I_2(t) = I_1(t) \cdot \exp\{-(t-\text{Delay})/\tau_2\}$$

5. Device according to claim 4,
characterized in that
said analyzer unit is designed for approximating a high-speed downward ramp of laser radiation after cut-off of pumping light, by the formula $$I_3(t) = I_2(t=\text{Delay}+t_e) \cdot \exp\{-(t-\text{Delay}-t_e)/\tau_3\}$$

6. Device according to claim 1,
characterized in that
said analyzer unit is designed for approximating a high-speed downward ramp of laser radiation after cut-off of pumping light, by the formula $$I_3(t) = I_2(t = \text{Delay} + t_e) \cdot \left[ \frac{\tau_{32}}{\tau_{32} - \tau_{31}} \cdot \exp\{-(t - \text{Delay} - t_e)/\tau_{32}\} - \frac{\tau_{31}}{\tau_{32} - \tau_{31}} \cdot \exp\{-(t - \text{Delay} - t_e))/\tau_{31}\} \right].$$

7. Device according to claim 1,
characterized in that
said analyzer unit is so designed that it takes approximations of an optical pulse as a basis for performing a convolution with model functions for heat transfer.

8. Device according to claim 1,
characterized in that
said analyzer unit is designed for performing a convolution of an optical pulse by means of a model function for heat transfer with application of a Cowan approximation.

9. Device according to claim 1,
characterized in that
said analyzer unit is designed for performing a convolution of an optical pulse by means of a model function for heat transfer for translucent materials.

10. Device according to claim 1,
characterized in that
said analyzer unit is designed for performing a convolution of an optical pulse by means of a model function for heat transfer with application of a Cape-Lehmann solution.

11. Device according to claim 1,
characterized in that
said analyzer unit is designed for performing a convolution of an optical pulse by means of a model function for heat transfer in multiple layers.

12. Device according to claim 1,
characterized in that
said analyzer unit is designed for performing a convolution of an optical pulse by means of a model function for heat transfer for multiple layers having thermal resistance.

\* \* \* \* \*

UNITED STATES PATENT AND TRADEMARK OFFICE
CERTIFICATE OF CORRECTION

PATENT NO.       : 7,038,209 B2
APPLICATION NO.  : 10/654780
DATED            : May 2, 2006
INVENTOR(S)      : Opfermann et al.

It is certified that error appears in the above-identified patent and that said Letters Patent is hereby corrected as shown below:

In the Claims

Claim 5 Col. 9

Line 21: the formula should read as follows:
$I_3(t) = I_2(Delay + t_e) \cdot \exp\{-Delay - t_e)/\tau_3\}$ Claim 6 Lines 30-31: the formula should read as follows:

$$I_3(t) = I_2(Delay + t_e) \cdot [\frac{\tau_{32}}{\tau_{32} - \tau_{31}} \cdot \exp\{-(t - Delay - t_e)/\tau_{32}\} - \frac{\tau_{31}}{\tau_{32} - \tau_{31}} \cdot \exp\{-(t - Delay - t_e))/\tau_{31}\}]$$

Signed and Sealed this

Sixteenth Day of January, 2007

JON W. DUDAS
*Director of the United States Patent and Trademark Office*